(12) United States Patent
Burrell et al.

(10) Patent No.: US 7,763,186 B2
(45) Date of Patent: *Jul. 27, 2010

(54) PREPARATION AND PURIFICATION OF IONIC LIQUIDS AND PRECURSORS

(75) Inventors: Anthony K. Burrell, Los Alamos, NM (US); Benjamin P. Warner, Los Alamos, NM (US); T. Mark McCleskey, Los Alamos, NM (US); Anoop Agrawal, Tucson, AZ (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/644,793

(22) Filed: Dec. 22, 2006

(65) Prior Publication Data

US 2007/0235696 A1  Oct. 11, 2007

Related U.S. Application Data

(60) Continuation-in-part of application No. 11/526,416, filed on Sep. 22, 2006, now Pat. No. 7,450,292, which is a continuation-in-part of application No. 11/041,069, filed on Jan. 20, 2005, now Pat. No. 7,119,937, which is a division of application No. 10/741,903, filed on Dec. 19, 2003, now Pat. No. 6,961,168, which is a continuation-in-part of application No. 10/600,807, filed on Jun. 20, 2003, now Pat. No. 6,853,472.

(60) Provisional application No. 60/390,611, filed on Jun. 21, 2002, provisional application No. 60/502,133, filed on Sep. 11, 2003.

(51) Int. Cl.
*H01B 1/00* (2006.01)

(52) U.S. Cl. .............. 252/500; 359/266; 359/321; 435/41; 546/24; 562/485

(58) Field of Classification Search ............ 252/500; 117/2; 359/266, 321; 423/464; 435/41; 546/24; 562/485
See application file for complete search history.

(56) References Cited

U.S. PATENT DOCUMENTS 4,053,571 A * 10/1977 Ebner et al. ............... 423/464

(Continued)

FOREIGN PATENT DOCUMENTS

JP        10-168028        6/1998

(Continued)

OTHER PUBLICATIONS

Rika Hagiwara and Yasuhiko Ito, "Room Temperature Ionic Liquids of Alkylimidazolium Cations and Fluoroanions," Journal of Fluorine Chemistry, vol. 105, pp. 221-227, Sep. 2000.

(Continued)

*Primary Examiner*—Randy Gulakowski
*Assistant Examiner*—Khanh Tuan Nguyen
(74) *Attorney, Agent, or Firm*—Samuel L. Borkowsky

(57) ABSTRACT

Substantially pure ionic liquids and ionic liquid precursors were prepared. The substantially pure ionic liquid precursors were used to prepare substantially pure ionic liquids.

4 Claims, 2 Drawing Sheets

U.S. PATENT DOCUMENTS

| | | | |
|---|---|---|---|
| 5,565,609 A * | 10/1996 | Hirowatari et al. | 562/485 |
| 5,827,602 A | 10/1998 | Koch et al. | |
| 5,923,456 A * | 7/1999 | Tench et al. | 359/266 |
| 6,319,428 B1 * | 11/2001 | Michot et al. | 252/500 |
| 6,365,068 B1 * | 4/2002 | Michot et al. | 252/500 |
| 6,365,301 B1 | 4/2002 | Michot et al. | |
| 6,531,270 B1 * | 3/2003 | Olson et al. | 430/391 |
| 6,552,843 B1 * | 4/2003 | Tench et al. | 359/321 |
| 6,703,507 B2 * | 3/2004 | Bahrmann et al. | 546/24 |
| 2004/0074842 A1 | 4/2004 | Mehnert et al. | |
| 2005/0005840 A1 * | 1/2005 | Bonrath et al. | 117/2 |
| 2006/0154328 A1 * | 7/2006 | Bruce et al. | 435/41 |

FOREIGN PATENT DOCUMENTS

| | | |
|---|---|---|
| WO | WO 01/93363 | 12/2001 |
| WO | WO 2004/080974 A1 * | 9/2004 |

OTHER PUBLICATIONS

Charles M. Gordon, "New Developments in Catalysis Using Ionic Liquids," Applied Catalysis A: General, vol. 222, pp. 101-117, Dec. 2001.

Martyn J. Earle, Paul B. McCormac, and Kenneth R. Seddon, "Diels-Alder Reactions in Ionic Liquids," Green Chemistry, pp. 23-25, Feb. 1999.

J. Sun, M. Forsyth, and D. R. MacFarlane, "Room-Temperature Molten Salts Based on the Quaternary Ammonium Ion," J. Phys. Chem. B. vol. 102, pp. 8858-8865, Oct. 1998.

P. Wasserscheid and T. Welton, editors, "Ionic Liquids in Synthesis," (2003), WILEY-VCH Verlag GmbH & Co. KGaA, Weinheim Germany, pp. 7-40.

Robinson et al., "An Electrochemical and Spectroscopic Study of Some Aromatic Hydrocarbons in the Room Temperature Molten Salt System Aluminum-Chloride-n-Butylpyridinium Chloride," J. Am. Chem. Soc., vol. 101, No. 2, Jan. 1979, pp. 323-327.

Paul et al., "How Transparent are the Imidazolium Ionic Liquids? A Case Study with 1-Methyl-3-Butylimidazolium Hexafluorophosphate, [bmim][PF$_6$]," Chem. Phys. Lett., vol. 402, Jan. 2005, pp. 375-379.

Paul et al., "Optical Absorption and Fluorescence Studies on Imidazolium Ionic Liquids Comprising the bis(trifluoromethanesulphonyl)imide Anion," J. Chem. Sci., vol. 118, Jul. 2006, pp. 335-340.

Hurley et al., "Electrodeposition of Metals from Fused Quaternary Ammonium Salts," vol. 98, No. 5, 1951, pp. 203-206.

Gifford et al., "A Substituted Imidazolium Chloroaluminate Molten Salt Possessing an Increased Electrochemical Window," J. Electrochem. Soc.: Electrochemical Science and Technology, vol. 134, No. 3, Mar. 1987, pp. 610-614.

Wilkes et al., "Air and Water Stable 1-Ethyl-3-methylimidazolium Based Ionic Liquids," J. Chem. Soc., Chem. Commun., 1992, pp. 965-967.

Bonhote et al., "Hydrophobic, Highly Conductive Ambient-Temperature Molten Salts," Inorg. Chem., vol. 35, 1996, pp. 1168-1178.

Huddleston et al.,"Room Temperature Ionic Liquids as Novel Media for Clean Liquid-liquid Extraction," Chem. Commun., 1998, pp. 1765-1766.

Muldoon et al., "Hydrogen Abstraction from Ionic Liquids by Benzophenone Triplet Excited States," Chem. Commun., 2001, pp. 2364-2365.

Cammarata et al., "Molecular States of Water in Room Temperature Ionic Liquids," Phys. Chem. Chem. Phys., vol. 3, issue 24, Dec. 2001, pp. 5192-5200.

Billard et al., "Stability of Divalent Europium in an Ionic Liquid: Spectroscopic Investigations in 1-Methyl-3-butylimidazolium Hexafluorophosphate," Inorganic Chemistry, vol. 42, No. 5, Mar. 2003, pp. 1726-1733.

Driesen et al., "Ionic Liquids as Solvents for Near-Infrared Emitting Lanthanide Complexes," Chemical Physics Letters, vol. 395, Sep. 2004, pp. 306-310.

Scammells et al., "Ionic Liquids: The Neglected Issues," Aust. J. Chem., vol. 58, Mar. 2005, 155-169.

Nockemann et al., "Purification of Imidazolium Ionic Liquids for Spectroscopic Applications," Chemical Physics Letters, vol. 415, Oct. 2005, pp. 131-136.

Mudring et al., "Strong Luminescence of Rare Earth Compounds in Ionic Liquids: Luminescent Properties of Lanthanide(III) Iodides in the Ionic Liquid 1-dodecyl-3-methylimidazolium bis(trifluoromethanesulfonyl)imide," Journal of Alloys and Compounds, vol. 418, Jul. 2006, pp. 204-208.

Crosthwaite et al., "Liquid Phase Behavior of Imidazolium-Based Ionic Liquids with Alcohols," J. Phys. Chem. B, vol. 108 (Apr. 2004) pp. 5113-5119.

Paul et al., "On the Optical Properties of the Imidazolium Ionic Liquids," J. Phys. Chem. B., vol. 109 (May 2005) pp. 9148-9153.

* cited by examiner

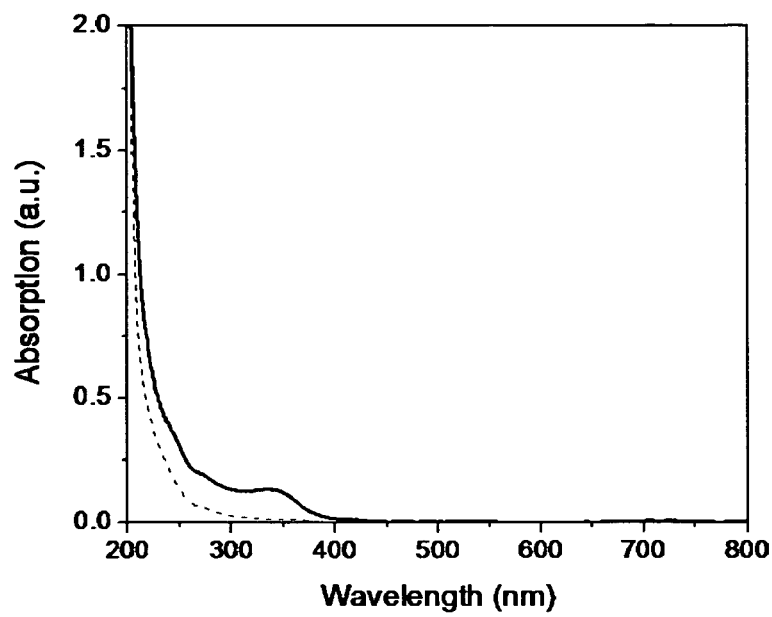
*Fig. 2*
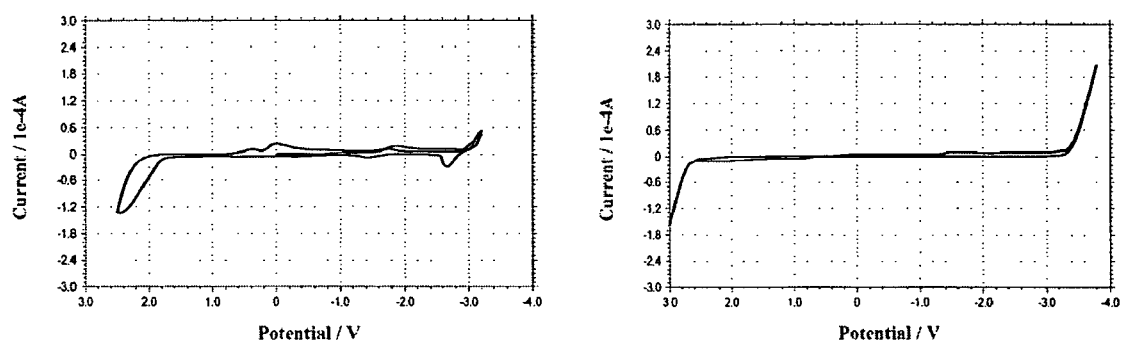
*Fig. 3a*  *Fig. 3b*

PREPARATION AND PURIFICATION OF IONIC LIQUIDS AND PRECURSORS

RELATED APPLICATIONS

This application is a continuation-in-part of U.S. patent application Ser. No. 11/526,416 filed Sep. 22, 2006 now U.S. Pat. No. 7,450,292 entitled "Durable Electrooptic Devices Comprising Ionic Liquids, which is a continuation-in-part of U.S. patent application Ser. No. 11/041,069 filed Jan. 20, 2005 entitled "Durable Electrooptic Devices Comprising Ionic Liquids, now issued as U.S. Pat. No. 7,119,937, which is a divisional of Ser. No. 10/741,903 filed Dec. 19, 2003 entitled "Durable Electrooptic Devices Comprising Ionic Liquids," now U.S. Pat. No. 6,961,168, which is a continuation-in-part of U.S. patent application Ser. No. 10/600,807 entitled "Electrolytes for Electrooptic Devices Comprising Ionic Liquids" filed Jun. 20, 2003, now U.S. Pat. No. 6,853,472, and claims priority of U.S. Provisional Patent Application 60/390,611 entitled "Electrolytes for Electrooptic Devices Comprising Ionic Liquids" filed Jun. 21, 2002, and U.S. Provisional Patent Application 60/502,133 entitled "Durable Electrooptic Devices" filed Sep. 11, 2003, all of which are incorporated by reference herein.

STATEMENT REGARDING GOVERNMENT RIGHTS

This invention was made with government support under Contract No. DE-AC51-06NA25396 awarded by the U.S. Department of Energy. The government has certain rights in the invention.

BACKGROUND

Ionic liquids are molten salts that have melting points at or below a temperature of 100° C. Ionic liquids are used in a wide variety of applications. Problems may arise when impure ionic liquids are used in devices and applications.

Substantially pure ionic liquids are not easily prepared using current methods. There remains a need for better methods for preparing substantially pure ionic liquids and ionic liquid precursors.

SUMMARY OF THE INVENTION

The invention includes a method for preparing ionic liquid substantially free of impurities. The method includes generating ionic liquid precursor comprising impurities; exposing the ionic liquid precursor to a purification agent comprising carbon, thereby substantially removing the impurities from the precursor and generating a purified ionic liquid precursor; and using the purified ionic liquid precursor to prepare ionic liquid.

The invention also includes an ionic liquid substantially free of impurities prepared by a method that includes generating ionic liquid precursor comprising impurities; exposing the ionic liquid precursor to a purification agent comprising carbon, thereby removing the impurities from the precursor; and using the purified precursor to prepare ionic liquid.

The invention also includes an ionic liquid substantially free of impurities prepared by a method that includes:

exposing an ionic liquid precursor to a purification agent comprising carbon, thereby removing the impurities, wherein said ionic liquid precursor comprises a cation of the formula

wherein R1 is selected from alkyl having 2-10 carbons, or a cation of the formula

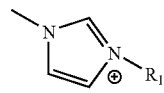

wherein $R_1$ is alkyl having 2-10 carbons. or a cation of the formula

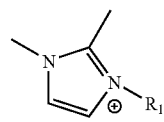

wherein $R_1$ is alkyl having 2-10 carbons or a cation of the formula

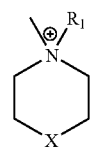

wherein $R_1$ is alkyl having 2-10 carbons and X is are independently selected from O and $CH_2$; and using the purified precursor to prepare ionic liquid.

The invention also includes a method for preparing ionic liquid. The method includes:

exposing an ionic liquid precursor to a purification agent comprising carbon, thereby removing the impurities, said ionic liquid precursor comprising a cation of the formula

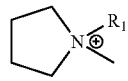

wherein R1 is selected from alkyl having 2-10 carbons, or a cation of the formula

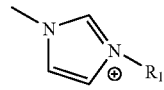

wherein $R_1$ is alkyl having 2-10 carbons. or a cation of the formula

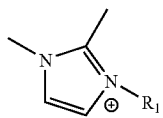

wherein $R_1$ is alkyl having 2-10 carbons or a cation of the formula

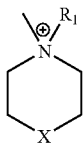

wherein $R_1$ is alkyl having 2-10 carbons and X is are independently selected from O and $CH_2$; and using the purified precursor to prepare ionic liquid.

The invention also includes a method for preparing ionic liquid substantially free of halide impurities. The method includes continuously extracting an aqueous ionic liquid phase into an organic solvent using a liquid-liquid extractor, the aqueous ionic liquid phase having halide impurities; separating the organic solvent and extracted ionic liquid therein from the aqueous phase; filtering the organic solvent and extracted ionic liquid therein through a material chosen from silica or alumina, thereby generating a filtrate; and removing organic solvent from the filtrate.

BRIEF DESCRIPTION OF THE DRAWINGS

The accompanying drawings are incorporated in and form a part of the specification, illustrate the embodiments of the present invention and, together with the description, serve to explain the principles of the invention. In the drawings:

FIG. 2 shows a ultraviolet-visible (UV-Vis) spectrum of neat commercially obtained (bold) 1-butyl-1-methylpyrrolidinum bis(trifluoromethanesulfonyl)amide, and a spectrum prepared according to an embodiment of the invention (dashed).

FIG. 3 shows the cyclic voltammagrams of commercially obtained neat 1-butyl-1-methylpyrrolidinum bis(trifluoromethanesulfonyl)amide (right), and cyclic voltammagram of neat 1-butyl-1-methylpyrrolidinum bis(trifluoromethanesulfonyl)amide prepared according to an embodiment of the invention (left).

DETAILED DESCRIPTION

Figure 1:
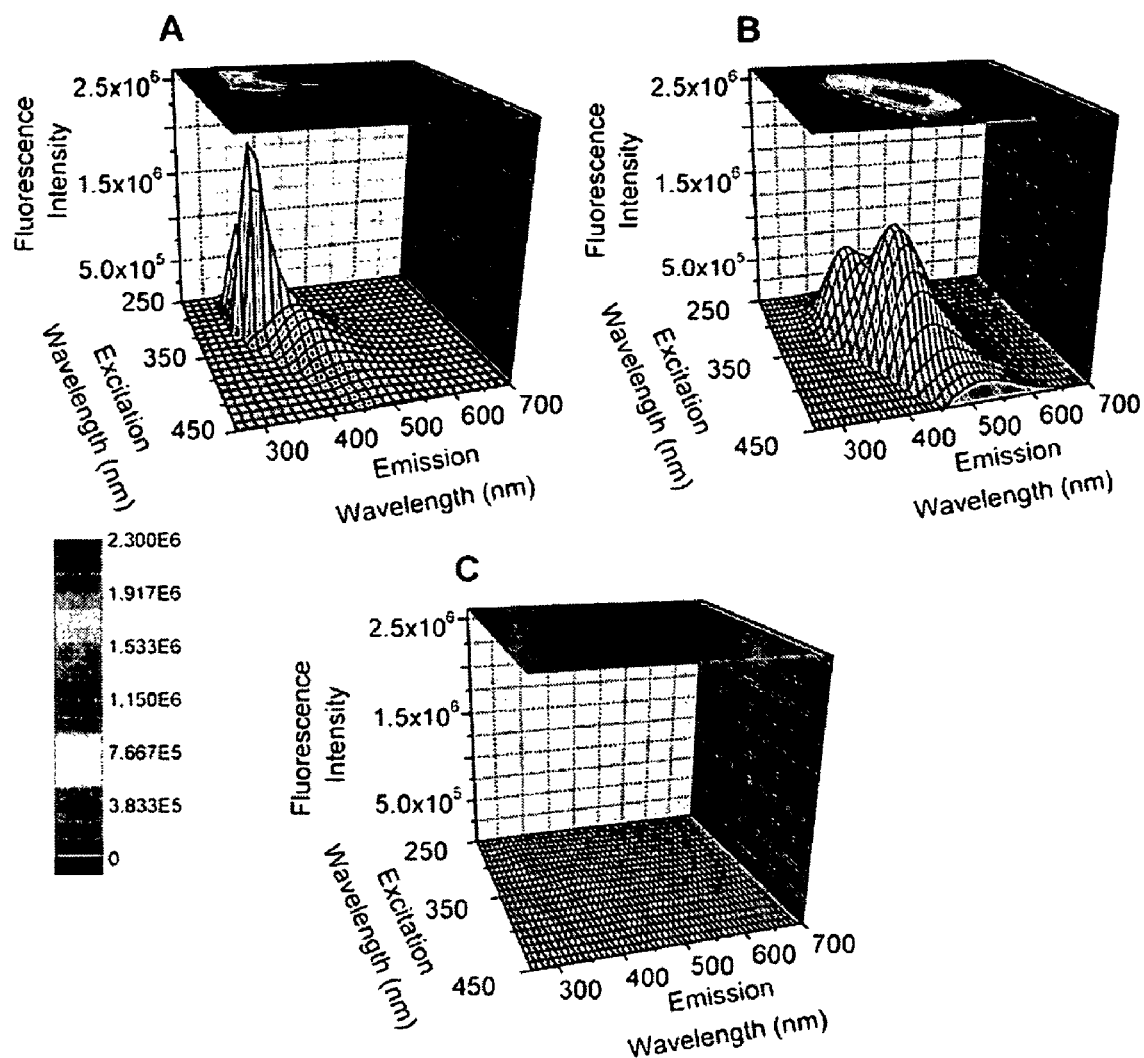
FIG. 1a and FIG. 1b show fluorescence spectra for commercially obtained samples of 1-butyl-3-methylimidazolium tetrafluoroborate.
FIG. 1c shows a fluorescence spectrum of a sample of 1-butyl-3-methylimidazolium tetrafluoroborate prepared according to an embodiment of the invention.

An aspect of the present invention is concerned with the preparation of substantially pure ionic liquid precursors, and substantially pure ionic liquids from the precursors. Purity being defined as the substantial absence of colored impurities as determined by UV-Vis spectroscopy with no substantial absorbance above 250 nm, no significant measurable current from impurities over the electrochemical window of the ionic liquid, or significant fluorescent impurities as determined by fluorescence spectroscopy. These substantially pure ionic liquids may be used in devices such as, but not limited to, electrooptic devices that employ ionic liquids as electrolyte solvents. Some non-limiting examples of ionic liquids that can be prepared in a substantially pure form according to embodiments of this invention include 1-ethyl-3-methylimidazolium chloride, 1-ethyl-3-methylimidazolium bromide, 1-butyl-3-methylimidazolium chloride, 1-butyl-3-methylimidazolium bromide, 1-butyl-1-methylpyrrolidinum chloride, 1-butyl-1-methylpyrrolidinum bromide, 1-butyl-2,3-dimethylimidazolium chloride, 1-butyl-2,3-dimethylimidazolium bromide, 1-butyl-3-methylimidazolium tetrafluoroborate, 1-ethyl-3-methylimidazolium tetrafluoroborate, 1-ethyl-3-methylimidazolium triflate, 1-butyl-3-methylimidazolium triflate, 1-butyl-2,3-dimethylimidazolium triflate, 1-butyl-1-methylpyrrolidinum tetrafluoroborate, 1-butyl-1-methylpyrrolidinum triflate, 1-ethyl-3-methylimidazolium bis(trifluoromethanesulfonyl)amide, 1-butyl-1-methylpyrrolidinum bis(trifluoromethanesulfonyl)amide, 1-butyl-3-methylimidazolium bis(trifluoromethanesulfonyl)amide, 1-butyl-1-methylpiperidinium tetrafluoroborate, 1-butyl-1-methylpiperidinium triflate, and 1-butyl-1-methylpiperidinium bis(trifluoromethanesulfonyl)amide.

Substantially pure ionic liquids prepared according to one or more aspects of the invention are non-volatile and provide high concentrations of cations and anions that offer minimal resistance to current.

Substantially pure ionic liquids that may be prepared according to embodiments of the invention include, but are not limited to, salts of organic cations in combination with either organic or inorganic anions. Some embodiment anions contain fluorine. Some of these anions include trifluoromethylsulfonate ("triflate," $CF_3SO_3^-$), bis(trifluoromethylsulfonyl)imide($N(CF_3SO_2)_2^-$), bis(perfluoroethylsulfonyl)imide ($(C_2F_5SO_2)_2N^-$)), tris(trifluoromethylsulfonyl)methide ($(CF_3SO_2)_3C^-$)). Others include tetrafluoroborate ($BF_4^-$), hexafluorophosphate ($PF_6^-$), hexafluoroantimonate ($SbF_6^-$), and hexafluoroarsenate ($AsF_6^-$). Bis(trifluoromethylsulfonyl)imide anion ($N(CF_3SO_2)_2^-$), for example, is inexpensive, has a high hydrophobicity, is sometimes referred to in the prior art as bis(trifluoromethanesulfonyl)amide or bis(trifluoromethanesulfonyl)imide, and has the structural formula

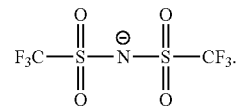

Some of the organic cations include, but are not limited to, pyridinium, pyridazinium, pyrimidinium, pyrazinium, imidazolium, pyrazolium, thiazolium, oxazolium, and triazolium.

A non-limiting list of quaternary ammonium-based ionic liquids that may be prepared in a substantially pure form according to aspects of this invention include those with a glass transition temperature ($T_g$) lower than about 40° C. that are 1-butyl-3-methylimidazolium tetrafluoroborate, 1-ethyl-3-methylimidazolium tetrafluoroborate, 1-ethyl-3-methylimidazolium triflate, 1-butyl-3-methylimidazolium triflate, 1-butyl-2,3-dimethylimidazolium triflate, 1-butyl-1-methylpyrrolidinum tetrafluoroborate, 1-butyl-1-methylpyrrolidinum triflate, 1-ethyl-3-methylimidazolium bis(trifluoromethanesulfonyl)amide, 1-butyl-1-methylpyrrolidinum bis(trifluoromethanesulfonyl)amide, 1-butyl-3-methylimidazolium bis(trifluoromethanesulfonyl)amide, 1-butyl-1-methylpiperidinium tetrafluoroborate, 1-butyl-1-methylpiperidinium triflate, and 1-butyl-1-methylpiperidinium bis (trifluoromethanesulfonyl)amide.

Some of the quaternary ammonium-based ionic liquids that can be prepared in a substantially pure form according to aspects of this invention are ionic liquids having tetraalkylammonium cations. Ionic liquids made from these cations have minimal optical absorbance in the ultraviolet portion of the spectrum, which gives molten salts based on these cations enhanced photochemical stability. Quaternary ammonium cations may be substituted with H, F, phenyl, alkyl groups with 1 to 15 carbon atoms, and other chemical substituents. Cations may even have bridged ring structures. Some of the quaternary ammonium cations are of the formula $(CH_3CH_2)_3N(R_1)$, wherein $R_1$ is alkyl having 2-10 carbons; or have the formula $(CH_3)_2(CH_3CHCH_3)N(R_2)$, wherein $R_2$ is alkyl having 2-10 carbons; or have the formula

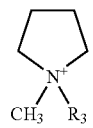

wherein $R_3$ is alkyl having 2-10 carbons;

or have the formula

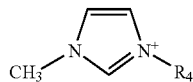

wherein $R_4$ is alkyl having 2-10 carbons.

In an embodiment, an ionic liquid that may be prepared in a substantially pure form is N-butyl-N-methylpyrrolidinium bis(trifluoromethylsulfonyl)imide.

Another aspect of the invention is concerned with the synthesis of substantially pure ionic liquids that do not significantly absorb ultraviolet radiation having a wavelength above 290 nanometers (nm), and therefore do not degrade when exposed to these wavelengths to byproducts that can lead to irreversible coloration, gas formation and/or formation of electrochemically active/inactive species.

Another aspect of the invention is concerned with the synthesis of substantially pure ionic liquids having a glass transition temperature Tg below about 0° C., a Tg below about minus 20 degrees Celsius (−20° C.), and a Tg below about minus 40° C. The glass transition temperature can be measured from the viscosity of the ionic liquid.

Another aspect of the invention is concerned with the synthesis of substantially halide-free ionic liquids using a continuous liquid-liquid extraction procedure. An aqueous solution of ionic liquid with halide impurities may be purified by continuously extracting out the ionic liquid in the organic solvent and leaving the halide impurities in the aqueous phase.

The following EXAMPLES demonstrate the operability of the invention.

Example 1

Purification of 1-ethyl-3-methylimidazolium bromide. A yellow solution of impure 1-ethyl-3-methylimidazolium bromide (ALDRICH) (50 grams (g)) having a yellow color in deionized water (250 mL) was prepared. Decolorizing charcoal (3 g) was added to the yellow solution and the resulting mixture was heated at 65° C. for 24 hours. The solution was cooled to room temperature and filtered. The filtrate was colorless. The water was removed from the colorless filtrate using a lyophilizer. The resulting solid was then heated under a vacuum for 48 hours at 65° C. The product white solid was substantially pure 1-ethyl-3-methylimidazolium bromide (48 g).

Example 2

Purification of 1-ethyl-3-methylimidazolium chloride. A yellow solution of impure 1-ethyl-3-methylimidazolium chloride (ALDRICH) (50 g) having a yellow color in deionized water (250 mL) was prepared. Decolorizing charcoal (3 g) was added to the yellow solution and the resulting mixture was heated at 65° C. for 24 hours. The solution was cooled to room temperature and filtered. The filtrate was colorless. The water was removed from the colorless filtrate using a lyophilizer. The resulting solid was then heated under a vacuum for 48 hours at 65° C. The product white solid was substantially pure 1-ethyl-3-methylimidazolium chloride (48 g).

Example 3

Purification of 1-ethyl-3-methylimidazolium chloride. A yellow solution of impure 1-ethyl-3-methylimidazolium chloride (ALDRICH) (50 grams) in deionized water (250 mL) was prepared. Decolorizing charcoal (3 g) was added to the yellow solution and the resulting mixture was heated at 65° C. for 24 hours. The solution was cooled to room temperature and filtered. The filtrate was pale yellow. The pale yellow solution then was treated with decolorizing charcoal (3 g). The mixture was heated for a further 24 hours at 65° C. The solution was cooled to room temperature and filtered. The filtrate was colorless. The water was removed from the colorless filtrate using a lyophilizer. The resulting solid was then heated under a vacuum for 48 hours at 65° C. The product white solid was substantially pure 1-ethyl-3-methylimidazolium chloride (48 g).

Example 4

Purification of 1-ethyl-3-methylimidazolium bromide. A yellow solution of impure 1-ethyl-3-methylimidazolium bromide (ALDRICH) (50 grams) having a yellow color in deionized water (250 mL) was prepared. Decolorizing charcoal (3 g) was added to the yellow solution and the resulting mixture was heated at 65° C. for 24 hours. The solution was cooled to room temperature and filtered. The filtrate was pale yellow. The yellow solution was treated with decolorizing charcoal (3 g). The mixture was heated for a further 24 hours at 65° C. The solution was cooled to room temperature and filtered. The filtrate was colorless. The water was removed from the colorless filtrate using a lyophilizer. The resulting solid was then heated under a vacuum for 48 hours at 65° C. The product white solid was substantially pure 1-ethyl-3-methylimidazolium bromide (48 g).

Example 5

Preparation of 1-butyl-3-methylimidazolium chloride. n-Chlorobutane (600 g) was added slowly to freshly distilled methylimidazole (500 g) in a two-liter, two-necked round bottom flask fitted with a reflux condenser. The resulting mixture was stirred with a magnetic stirrer at 70° C. for 1 week. During the week a white solid formed, which slowly turned yellow. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This mixture was heated to 70° C. for 24 hours, cooled and filtered. The filtrate was colorless. The water was then removed from the colorless filtrate using a lyophilizer. The resulting solid was then heated under high vacuum for 48 hours at 65° C., and then cooled. 1-butyl-3-methylimidazolium chloride was obtained as a white solid in a yield of 92%.

Example 6

Preparation of 1-butyl-3-methylimidazolium chloride. n-Chlorobutane (600 g) was added slowly to freshly distilled methylimidazole (500 g) in a two-liter, two-necked round bottom flask fitted with a reflux condenser. The resulting mixture was stirred with a magnetic stirrer at 70° C. for 1 week. During the week a white solid formed, which slowly turned yellow. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This mixture was heated to 70° C. for 24 hours, cooled and filtered. The filtrate was pale yellow. The pale yellow filtrate was then treated with decolorizing charcoal (30 g). The mixture was heated for a further 24 hours at 65° C. The mixture was cooled to room temperature and filtered. The filtrate was colorless. The water was removed from the colorless filtrate using a lyophilizer. The resulting solid was then heated under a vacuum for 48 hours at 65° C. The white solid was substantially pure 1-butyl-3-methylimidazolium chloride was obtained as a white solid in a yield of 92%.

Example 7

Preparation of 1-butyl-3-methylimidazolium bromide. n-Bromobutane (860 g) was added slowly to freshly distilled methylimidazole (500 g) in a two-liter, two-necked round bottom flask fitted with a reflux condenser. The addition was at such a rate that the temperature of the solution did not get above 40° C. This mixture was then stirred with a magnetic stirrer at room temperature for 1 day. During this time a yellow solid formed. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This mixture was heated to 70° C. for 24 hours, cooled and filtered. The filtrate was colorless. The water was then removed using a lyophilizer. The resulting solid was then heated under high vacuum for 48 hours at 65° C., and then cooled. 1-Butyl-3-methylimidazolium bromide was obtained as a white solid in 94% yield.

Example 8

Preparation of 1-butyl-3-methylimidazolium bromide. n-Bromobutane (860 g) was added slowly to freshly distilled methylimidazole (500 g) in a two-liter, two-necked round bottom flask fitted with a reflux condenser. The addition was at such a rate that the temperature of the solution did not get above 40° C. This mixture was then stirred with a magnetic stirrer at room temperature for 1 day. During this time a yellow solid formed. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This mixture was heated to 70° C. for 24 hours, cooled and filtered. The filtrate was pale yellow. The yellow solution was then treated with decolorizing charcoal (30 g). The mixture was heated for a further 24 hours at 65° C. The solution was cooled to room temperature and filtered. The filtrate was colorless. The water was then removed using a lyophilizer. The resulting solid was then heated under high vacuum for 48 hours at 65° C., and then cooled. 1-Butyl-3-methylimidazolium bromide was obtained as a white solid in 94% yield.

Example 9

Preparation of 1-butyl-1-methylpyrrolidinum chloride. n-Chlorobutane (570 g) was added slowly added to freshly distilled methylpyrrolidine (500 g) in a two-liter, two-necked round bottom flask fitted with a reflux condenser. This mixture was then stirred with a magnetic stirrer at 70° C. for 1 week. During the week a white solid formed, which slowly turned yellow. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This solution was heated to 70° C. for 24 hours, cooled and filtered. The filtrate was colorless. The water was then removed using a lyophilizer. The resulting solid was then heated under high vacuum for 48 hours at 65° C., and then cooled. 1-Butyl-1-methylpyrrolidinum chloride was obtained as a white solid in 89% yield.

Example 10

Preparation of 1-butyl-1-methylpyrrolidinum chloride. n-Chlorobutane (570 g) was added slowly added to freshly distilled methylpyrrolidine (500 g) in a two-liter, two-necked round bottom flask fitted with a reflux condenser. This mixture was then stirred with a magnetic stirrer at 70° C. for 1 week. During the week a white solid formed, which slowly turned yellow. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This solution was heated to 70° C. for 24 hours, cooled and filtered. The filtrate was pale yellow. The pale yellow filtrate was then treated with decolorizing charcoal (30 g). The mixture was heated for a further 24 hours at 65° C. The solution was cooled to room temperature and filtered. The filtrate was colorless. The water was then removed using a lyophilizer. The resulting solid was then heated under high vacuum for 48 hours at 65° C., and then cooled. 1-Butyl-1-methylpyrrolidinum chloride was obtained as a white solid in 89% yield.

Example 11

Preparation of 1-butyl-1-methylpyrrolidinum bromide. n-Bromobutane (900 g) was added slowly to freshly distilled methylpyrrolidine (500 g) in a 2 L two necked round bottom flask fitted with a reflux condenser. The addition was at such a rate that the temperature of the solution did not get above 40° C. This mixture was then stirred with a magnetic stirrer for 1 day to give a yellow solid. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This solution was heated to 70° C. for 24 hours, cooled and filtered. The filtrate was colorless. The water was then removed using a lyophilizer. The resulting solid was then heated under high vacuum for 48 hours at 65° C., and then cooled. 1-Butyl-1-methylpyrrolidinum bromide was recovered as a white solid in 91% yield.

Example 12

Preparation of 1-butyl-1-methylpyrrolidinum bromide. n-Bromobutane (900 g) was added slowly to freshly distilled methylpyrrolidine (500 g) in a 2 L two necked round bottom flask fitted with a reflux condenser. The addition was at such a rate that the temperature of the solution did not get above 40° C. This mixture was then stirred with a magnetic stirrer for 1 day to give a yellow solid. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (30 g) was added. This solution was heated to 70° C. for 24 hours, cooled and filtered. The filtrate was pale yellow. The pale yellow filtrate was then treated with decolorizing charcoal (30 g). The mixture was heated for a further 24 hours at 65° C. The solution was cooled to room temperature and filtered. The filtrate was colorless. The water was then removed using a lyophilizer. The resulting solid was then heated under high vacuum for 48 hours at 65° C., and then cooled. 1-Butyl-1-methylpyrrolidinum bromide was recovered as a white solid in 91% yield.

Example 13

Preparation of 1-butyl-2,3-dimethylimidazolium chloride. n-Chlorobutane (55 g) was added slowly to 1,2-dimethylimidazole (50 g) in a 200-milliliter, two-necked round bottom flask fitted with a reflux condenser. This mixture was then stirred with a magnetic stirrer at 70° C. for 1 week. During the week a white solid formed, which slowly turned yellow. The solution was allowed to cool to room temperature. The liquid was decanted away from the yellow solid that remained. The yellow solid washed with diethylether (3×200 mL) and dried under vacuum for 24 hours. The dry yellow solid was dissolved in water (1.5 liters) and decolorizing charcoal (6 g) was added. This mixture was heated to 70° C. for 24 hours, cooled and filtered. The filtrate was pale yellow. The pale yellow filtrate was then treated with decolorizing charcoal (6 g). The mixture was heated for a further 24 hours at 65° C. The solution was cooled to room temperature and filtered. The filtrate was colorless. The water was removed from the colorless filtrate using a lyophilizer. The resulting solid was then heated under a vacuum for 48 hours at 65° C. 1-Butyl-2,3-dimethylimidazolium chloride was obtained as a white solid in a yield of 85%.

Example 14

Preparation of 1-butyl-2,3-dimethylimidazolium bromide. n-Bromobutane (80 g) was added slowly to 1,2-dimethylimidazole (50 g) in a 200 mL two necked round bottom flask fitted with a reflux condenser. The addition was at such a rate that the temperature of the solution did not get above 40° C. This mixture was then stirred with a magnetic stirrer for 1 day to give a yellow solid. The dry yellow solid was dissolved in water (1.5 liters) and decolorizing charcoal (10 g) was added. This mixture was heated to 70° C. for 24 hours, cooled and filtered. The filtrate was pale yellow. The yellow solution was then treated with decolorizing charcoal (10 g). The mixture was heated for a further 24 hours at 65° C. The solution was cooled to room temperature and filtered. The filtrate was colorless. The water was removed from the colorless filtrate using a lyophilizer. The resulting solid was then heated under a vacuum for 48 hours at 65° C. 1-Butyl-2,3-dimethylimidazolium bromide was obtained as a white solid in a yield of 98% yield.

Example 15

Preparation of 1-butyl-3-methylimidazolium tetrafluoroborate. n-Bromobutane (600 g) was added slowly to freshly distilled methylimidazole (500 g) in a 2 L two necked round bottom flask fitted with a reflux condenser. The addition was at such a rate that the temperature of the solution did not get above 40° C. This mixture was then stirred with a magnetic stirrer at room temperature for 1 day. During this time a yellow solid forms. This solid was filtered and washed with diethylether (3×200 mL) then dried under vacuum. The yellow solid was then dissolved in deionized water (1.5 L). Decolorizing charcoal (30 g) was added to the solution and the resulting mixture heated at 65° C. for 24 hours. The mixture was then cooled to room temperature and filtered. The clean 1-butyl-3-methylimidazolium bromide solution was then poured into a solution of sodium tetrafluoroborate (680 g) in 1000 mL of deionized water. The solution was then stirred at room temp for 3 hrs. The solution was then transferred to a continuous liquid-liquid extractor and extracted with dichloromethane for 48 hours. The dichloromethane solution was filtered through a plug of silica (100 g), and then the dichloromethane was removed under vacuum to give the neat 1-butyl-3-methylimidazolium tetrafluoroborate. The dichloromethane solution was filtered through a plug of silica and the dichloromethane removed under vacuum. The colorless, 1-butyl-3-methylimidazolium tetrafluoroborate was obtained in >95% yield even with repeated liquid-liquid extractions.

Example 16

Preparation of halide free 1-butyl-3-methylimidazolium tetrafluoroborate. 1-Butyl-3-methylimidazolium tetrafluoroborate (50 g) prepared as in EXAMPLE 15 was dissolved in water (100 mL) and extracted in the liquid-liquid extractor with dichloromethane for 48 hours. The dichloromethane solution was filtered through a plug of silica and the dichloromethane removed under vacuum. This process was repeated 3 times. The ionic liquid gave a negative bromide test using silver nitrate solution. The colorless, bromide free 1-butyl-3-methylimidazolium tetrafluoroborate was obtained in >95%

Example 17

Preparation of 1-ethyl-3-methylimidazolium tetrafluoroborate. A solution of 1-ethyl-3-methylimidazolium bromide (50 g) in deionized water (200 mL) was prepared. Decolorizing charcoal (3 g) was added to the solution and the resulting mixture was heated at 65° C. for 24 hours. The mixture was then cooled to room temperature and filtered. The colorless solution containing the 1-ethyl-3-methylimidazolium bromide was then poured into a solution of sodium tetrafluoroborate (30 g) in 200 mL of deionized water. The solution was then stirred at room temperature for 3 hours. The solution was then transferred to a continuous liquid-liquid extractor and extracted with dichloromethane for 48 hours. The dichloromethane solution was filtered through a plug of silica (100 g), and then the dichloromethane was removed under vacuum to give the neat colorless, 1-ethyl-3-methylimidazolium tetrafluoroborate in greater than 90% yield.

Example 18

Preparation of halide free 1-ethyl-3-methylimidazolium tetrafluoroborate. 1-Ethyl-3-methylimidazolium tetrafluoroborate (50 g) prepared as in EXAMPLE 17 was dissolved in water (100 mL) and extracted in the liquid-liquid extractor with dichloromethane for 48 hours. The dichloromethane solution was filtered through a plug of silica and the dichloromethane removed under vacuum. This process was repeated 3 times. The ionic liquid gave a until a negative bromide test using silver nitrate solution. The colorless, bromide free 1-Butyl-3-methylimidazolium tetrafluoroborate was obtained in >95%.

The fluorescence spectra of two commercial samples of 1-butyl-3-methylimidazolium tetrafluoroborate are shown in FIG. 1a and FIG. 1b, and a sample prepared according to EXAMPLE 17 and 18 is shown in FIG. 1c. As FIG. 1 shows, the commercial samples have some amount of fluorescence emission indicating the presence of fluorescent impurities, while the embodiment sample of the invention does not fluoresce, indicating the absence of fluorescent impurities.

Example 19

Preparation of 1-ethyl-3-methylimidazolium triflate. A solution of impure 1-Ethyl-3-methylimidazolium bromide (50 g) in deionized water (200 mL) was prepared. Decolorizing charcoal (3 g) was added to the solution and the resulting mixture heated at 65° C. for 24 hours. The mixture was then cooled to room temperature and filtered. The clean 1-ethyl-3-methylimidazolium bromide solution was then poured into a solution of sodium triflate (50 g) in 200 mL of deionized water. The solution was then stirred at room temperature for 3 hrs. The solution was then transferred to a continuous liquid-liquid extractor and extracted with dichloromethane for 48 hours. The dichloromethane solution was filtered through a plug of silica (10 g), and then the dichloromethane was removed under vacuum to give the neat colorless, 1-ethyl-3-methylimidazolium triflate was obtained in >95% yield.

Example 20

Preparation of halide free 1-ethyl-3-methylimidazolium triflate. 1-ethyl-3-methylimidazolium triflate (50 g) prepared as in EXAMPLE 19 was dissolved in water (100 mL) and extracted in the liquid-liquid extractor with dichloromethane for 48 hours. The dichloromethane solution was filtered through a plug of silica and the dichloromethane removed under vacuum. This process was repeated 3 times. The ionic liquid gave a negative bromide test. The colorless, bromide free 1-ethyl-3-methylimidazolium triflate was obtained in >95%

Example 21

Preparation of 1-Butyl-3-methylimidazolium triflate. n-Bromobutane (60 g) was added slowly to freshly distilled methylimidazole (50 g) in a 2-liter, two-necked round bottom flask fitted with a reflux condenser. The addition was at a rate such that the temperature of the mixture did not get above 40° C. This mixture was then stirred with a magnetic stirrer at room temperature for 1 day. During this time a yellow solid forms. This solid was filtered and washed with diethylether (3×20 mL) then dried under vacuum. The yellow solid was then dissolved in deionized water 100 mL. Decolorizing charcoal (3 g) was added to the solution and the resulting mixture heated at 65° C. for 24 hours. The mixture was then cooled to room temperature and filtered. The solution became colorless. The colorless solution was then poured into a solution of sodium triflate (110 g) in 200 mL of deionized water. The solution was then stirred at room temperature for 3 hrs. The solution was then transferred to a continuous liquid-liquid extractor and extracted with dichloromethane for 48 hours. The dichloromethane solution was filtered through a plug of silica (20 g), and then the dichloromethane was removed under vacuum to give the neat colorless, 1-butyl-3-methylimidazolium triflate in >95% yield.

Example 22

Preparation of halide free 1-butyl-3-methylimidazolium triflate. 1-butyl-3-methylimidazolium triflate (50 g) prepared as in EXAMPLE 21 was dissolved in water (100 mL) and extracted in the liquid-liquid extractor with dichloromethane for 48 hours. The dichloromethane solution was filtered through a plug of silica and the dichloromethane removed under vacuum. This process was repeated 3 times. The ionic liquid gave a negative bromide test. The colorless, bromide free 1-butyl-3-methylimidazolium triflate was obtained in >95%

Example 23

Preparation of 1-Butyl-2,3-dimethylimidazolium triflate. n-Bromobutane (60 g) was added slowly to freshly distilled 1,2-dimethylimidazole (50 g) in a 2-liter, two-necked round bottom flask fitted with a reflux condenser. The addition was at a rate such that the temperature of the mixture did not get above 40° C. This mixture was then stirred with a magnetic stirrer at room temperature for 1 day. During this time a yellow solid forms. This solid was filtered and washed with diethylether (3×20 mL) then dried under vacuum. The yellow solid was then dissolved in deionized water 100 mL. Decolorizing charcoal (3 g) was added to the solution and the resulting mixture heated at 65° C. for 24 hours. The mixture was then cooled to room temperature and filtered. The solution became colorless. The colorless solution was then poured into a solution of sodium triflate (110 g) in 200 mL of deionized water. The solution was then stirred at room temperature for 3 hrs. The solution was then transferred to a continuous liquid-liquid extractor and extracted with dichloromethane for 48 hours. The dichloromethane solution was filtered through a plug of silica (20 g), and then the dichloromethane was removed under vacuum to give the solid colorless, 1-Butyl-2,3-dimethylimidazolium triflate was obtained in >90% yield.

Example 24

Preparation of 1-butyl-1-methylpyrrolidinum tetrafluoroborate. N-Bromobutane (60 g) was added slowly to freshly distilled methylpyrrolidine (50 g) in a 2-liter, two-necked round bottom flask fitted with a reflux condenser. The addition was at a rate such that the temperature of the mixture did not get above 40° C. This mixture was then stirred with a magnetic stirrer at room temperature for 1 day. During this time a yellow solid forms. This solid was filtered and washed with diethylether (3×20 mL) then dried under vacuum. The yellow solid was then dissolved in deionized water 100 mL. Decolorizing charcoal (3 g) was added to the solution and the resulting mixture heated at 65° C. for 24 hours. The mixture was then cooled to room temperature and filtered. The filtrate was colorless. The colorless filtrate was then poured into a solution of sodium tetrafluoroborate (10 g) in 200 mL of deionized water. The solution was then stirred at room temperature for 3 hrs. The solution was then transferred to a continuous liquid-liquid extractor and extracted with dichloromethane for 48 hours. The dichloromethane solution was filtered through a plug of silica (20 g), and then the dichloromethane was removed under vacuum to give the solid colorless, 1-butyl-1-methylpyrrolidinum tetrafluoroborate was obtained in >90% yield.

Example 25

Preparation of 1-butyl-1-methylpyrrolidinum triflate. n-Bromobutane (60 g) was added slowly to freshly distilled methylpyrrolidine (50 g) in a 2-liter, two-necked round bottom flask fitted with a reflux condenser. The addition was at a rate such that the temperature of the mixture did not get above 40° C. This mixture was then stirred with a magnetic stirrer at room temperature for 1 day. During this time a yellow solid forms. This solid was filtered and washed with diethylether (3×20 mL) then dried under vacuum. The yellow solid was then dissolved in deionized water 100 mL. Decolorizing charcoal (3 g) was added to the solution and the resulting mixture heated at 65° C. for 24 hours. The mixture was then cooled to room temperature and filtered. The filtrate was colorless. The colorless filtrate was then poured into a solution of sodium triflate (110 g) in 200 mL of deionized water. The solution was then stirred at room temperature for 3 hours. The solution was then transferred to a continuous liquid-liquid extractor and extracted with dichloromethane for 48 hours. The dichloromethane solution was filtered through a plug of silica (20 g), and then the dichloromethane was removed under vacuum to give the colorless, 1-butyl-1-methylpyrrolidinum triflate. was obtained in >90% yield.

Example 26

Preparation of 1-ethyl-3-methylimidazolium bis(trifluoromethanesulfonyl)amide. Yellow 1-ethyl-3-methylimidazolium chloride (Aldrich) (50 g) was dissolved in deionized water (250 mL). Decolorizing charcoal (3 g) was added to the solution and the resulting mixture heated at 65° C. for 24 hours. The solution was cooled to room temperature and filtered. The colorless filtrate was poured into a solution of lithium bis(trifluoromethanesulfonyl)amide (115 g) in 200 mL of deionized water. The solution was then stirred at room temperature for 3 hours after which two layers had formed. The bottom layer was separated and washed three times with deionized water (100 mL). The layer was then heated at 65° C. under vacuum for 48 hours and then filtered through activated alumina to give 1-ethyl-3-methylimidazolium bis(trifluoromethanesulfonyl)amide as a colorless clean dry material in 89% yield.

Example 27

Preparation of 1-ethyl-3-methylimidazolium bis(trifluoromethanesulfonyl)amide. Yellow 1-ethyl-3-methylimidazolium chloride (Aldrich) (50 g) was dissolved in deionized water (250 mL). Decolorizing charcoal (3 g) was added to the solution and the resulting mixture heated at 65° C. for 24 hours. The solution was cooled to room temperature and filtered. To the yellow filtrate was added decolorizing charcoal (3 g) and the solution was then heated for a further 24 hours at 65° C. The solution was allowed to cool to room temperature and then filtered to give a colorless solution. This solution was poured into a solution of lithium bis(trifluoromethanesulfonyl)amide (115 g) in 200 mL of deionized water. The solution was then stirred at room temperature for 3 hrs after which two layers had formed. The bottom layer was separated and washed three times with deionized water (100 mL). The layer was then heated at 65° C. under vacuum for 48 hrs and then filtered through activated alumina to give 1-ethyl-3-methylimidazolium bis(trifluoromethanesulfonyl) amide as a colorless clean dry material in 87% yield.

Example 28

Preparation of 1-butyl-1-methylpyrrolidinum bis(trifluoromethanesulfonyl)amide. n-Bromobutane (900 g) was slowly added to freshly distilled methylpyrrolidine (500 g) in a 2 L two necked round bottom flask fitted with a reflux condenser. The addition was added at such a rate that the temperature of the solution did not get above 40° C. This mixture was then stirred with a magnetic stirrer at room temperature for 1 day. During this time a yellow solid forms. This solid was filtered and washed with ether (3×200 mL) then dried under vacuum. The yellow solid was then dissolved deionized water (1 L). Decolorizing charcoal (30 g) was added to the solution and the resulting mixture heated at 65° C. for 24 hours. The mixture was then cooled to room temperature and filtered. To the yellow filtrate was added decolorizing charcoal (30 g) and the solution was then heated for a further 24 hours at 65° C. The solution was allowed to cool to room temperature and then filtered to give a colorless solution. The clean 1-butyl-1-methylpyrrolidinum bromide solution was then poured into a solution of lithium bis(trifluoromethanesulfonyl)amide (1800 g) in deionized water (2 L). The solution was then stirred at room temperature for 3 hrs after which two layers had formed. The bottom layer was separated and washed three times with deionized water (500 mL). The 1-butyl-1-methylpyrrolidinum bis(trifluoromethanesulfonyl)amide was then heated at 65° C. under vacuum (0.1 mbar) for 48 hrs and then filtered through activated alumina to give colorless clean dry material (89% yield).

A Ultraviolet-Visible (UV-V is) spectrum of commercial high purity grade (MERCK) neat 1-butyl-1-methylpyrrolidinum bis(trifluoromethanesulfonyl)amide (bold) and a sample of 1-butyl-1-methylpyrrolidinum bis(trifluoromethanesulfonyl)amide prepared in our laboratory (dashed) is shown in FIG. 2.

Cyclic voltammagrams (CV) of neat 1-butyl-1-methylpyrrolidinum bis(trifluoromethanesulfonyl)amide are shown in FIG. 3a-b. FIG. 3b shows a CV of a commercially obtained sample (MERCK), while FIG. 3a is a sample prepared according to this EXAMPLE. The CVs were obtained using a platinum working electrode, platinum counter electrode and a silver reference electrode scanned at 50 mV/s. As FIG. 3 shows, the commercially obtained sample includes detectable impurities, while the sample prepared according to this EXAMPLE does not. More generally, ionic liquids prepared according to this invention are important from a commercial perspective because the presence of impurities in commercial samples increases side reactions and hence are undesirable for durability (including cyclic durability) of electrochemical devices such as their use in electrolytes for electrochromic devices, electroluminescent devices, batteries, sensors and super-capacitors. For optical devices such as electrochromic and electroluminescent devices, the use of ionic liquids prepared according to this invention results in improvements in properties where devices are exposed to solar optical radiation, for example, UV and visible light. Many of such optical devices have shown potential to be used as displays, labels, automotive mirrors and windows for use in architectural and transportation use. In addition such ionic liquids can be used for chemical and electrochemical synthesis of materials. Substantially pure ionic liquids prepared according to this invention will result in increased product yields and increased product purity.

Example 29

Preparation of 1-Butyl-1-methylpyrrolidinum bis(trifluoromethanesulfonyl)amide. n-Bromobutane (900 g) was slowly added to freshly distilled methylpyrrolidine (500 g) in a 2 L two necked round bottom flask fitted with a reflux condenser. The addition was added at such a rate that the temperature of the solution did not get above 40° C. This mixture was then stirred with a magnetic stirrer at room temperature for 1 day. During this time a yellow solid forms. This solid was filtered and washed with ether (3×200 mL) then dried under vacuum. The yellow solid was then dissolved deionized water (1 L). Decolorizing charcoal (30 g) was added to the solution and the resulting mixture heated at 65° C. for 24 hours. The mixture was then cooled to room temperature and filtered. The clean 1-butyl-1-methylpyrrolidinum bromide solution was then poured into a solution of lithium bis(trifluoromethanesulfonyl)amide (1800 g) in deionized water (2 L). The solution was then stirred at room temperature for 3 hours after which two layers had formed. The bottom layer was separated and washed three times with deionized water (500 mL). The 1-butyl-1-methylpyrrolidinum bis(trifluoromethanesulfonyl)amide was then heated at 65° C. under vacuum (0.1 mbar) for 48 hrs and then filtered through activated alumina to give colorless clean dry material (89% yield).

Example 30

Preparation of 1-butyl-3-methylimidazolium bis(trifluoromethanesulfonyl)amide. n-Bromobutane (860 g) was slowly added to freshly distilled methylimidazole (500 g) in a 2 L two necked round bottom flask fitted with a reflux condenser. The addition was added at such a rate that the temperature of the solution did not get above 40° C. This mixture was then stirred with a magnetic stirrer at room temperature for 1 day. During this time a yellow solid forms. This solid was filtered and washed with ether (3×200 mL) then dried under vacuum. The yellow solid was then dissolved deionized water (1 L). Decolorizing charcoal (30 g) was added to the solution and the resulting mixture heated at 65° C. for 24 hours. The mixture was then cooled to room temperature and filtered. At this point the solution should be colorless. The clean 1-butyl-3-methylimidazolium bromide solution was then poured into a solution of lithium bis(trifluoromethanesulfonyl)amide (1850 g) in 2 L of deionized water. The solution was then stirred at room temperature for 3 hrs after which two layers had formed. The bottom layer was separated and washed three times with deionized water (500 mL). The 1-butyl-3-methylimidazolium bis(trifluoromethanesulfonyl) amide was then heated at 65° C. under vacuum for 48 hours and then filtered through activated alumina to give clean dry material in 89% yield.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing a substantially nonfluorescent composition comprising ionic liquid that is a molten salt having a melting temperature at or below 100° C., comprising:

heating a compound of the formula [cation-1][X] with charcoal or activated carbon, wherein X is a halide and [cation-1] is a quaternary ammonium cation of the formula

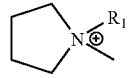

wherein R1 is selected from alkyl having 2-10 carbons, or a cation of the formula

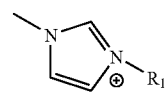

wherein $R_1$ is alkyl having 2-10 carbons, or a cation of the formula

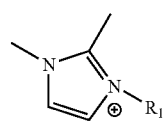

wherein $R_1$ is alkyl having 2-10 carbons or a cation of the formula

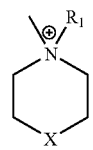

wherein $R_1$ is alkyl having 2-10 carbons and X is are independently selected from O and $CH_2$; and thereafter reacting the [cation-1][X] compound with a compound of the formula [cation-2] [Y] wherein [cation-2] is a cation and wherein [Y] is $BF_4^-$, $PF_6^-$, trifluoromethylsulfonate ($CF_3SO_3^-$), bis(trifluoromethylsulfonyl)imide (($CF_3SO_2)_2N^-$), bis(perfluoroethylsulfonyl)imide ((CF₃CF₂SO₂)₂N⁻), or tris(trifluoromethylsulfonyl)methide ((CF₃SO₂)₃C⁻), thereby forming a substantially nonfluorescent composition comprising ionic liquid that is a molten salt having a melting temperature at or below 100° C.

2. The method of claim 1, wherein the ionic liquid has a measured absorbance of less than 0.15 absorbance units for wavelengths in the range from about 350 nanometers to about 750 nanometers for a sample having a path length of about 1 centimeter.

3. A substantially nonfluorescent, white or colorless composition comprising a white or colorless ionic liquid of the formula [cation-2][Y] wherein [cation-2] is a quaternary ammonium cation of the formula

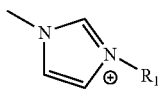

wherein $R_1$ is alkyl having 2-10 carbons
or a quaternary ammonium cation of the formula

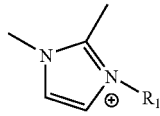

wherein $R_1$ is alkyl having 2-10 carbons and [Y] is BF₄⁻, PF₆⁻, trifluoromethylsulfonate (CF₃SO₃⁻), bis(trifluoromethylsulfonyl)imide ((CF₃SO₂)₂N⁻), bis(perfluoroethylsulfonyl)imide ((CF₃CF₂SO₂)₂N⁻), and tris(trifluoromethylsulfonyl)methide ((CF₃SO₂)₃C⁻).

4. The ionic liquid of claim 3, wherein said ionic liquid has a measured absorbance of less than 0.15 absorbance units for wavelengths in the range from about 350 nanometers to about 750 nanometers for a sample having a path length of about 1 centimeter.

* * * * *